(12) United States Patent
Floyd

(10) Patent No.: US 6,444,880 B1
(45) Date of Patent: Sep. 3, 2002

(54) STABLE INTERMEDIATE RYEGRASS VARIETIES

(75) Inventor: Donald Floyd, Albany, OR (US)

(73) Assignee: Pickseed West, Inc., Tangent, OR (US)

( * ) Notice: Subject to any disclaimer, the term of this patent is extended or adjusted under 35 U.S.C. 154(b) by 0 days.

(21) Appl. No.: 09/624,046

(22) Filed: Jul. 24, 2000

(51) Int. Cl.[7] .............................. A01H 1/00; A01H 5/00
(52) U.S. Cl. ........................................ 800/320; 800/260
(58) Field of Search ................................. 800/320, 260

(56) References Cited

PUBLICATIONS

Schmitz, J., "A Smooth Transition," *Golf Course Management,* Jul., 1999, pages unknown, USA.

*Primary Examiner*—Bruce R. Campell
*Assistant Examiner*—A Para
(74) *Attorney, Agent, or Firm*—Rothwell, Figg, Ernst & Manbeck

(57) ABSTRACT

Uniform and stable varieties of intermediate ryegrass that have characteristics desired for a turfgrass including plant height, leaf texture, flag leaf width, seedling vertical growth rate and turf density.

12 Claims, No Drawings

STABLE INTERMEDIATE RYEGRASS VARIETIES

FIELD OF THE INVENTION

This invention relates to cultivated varieties of true breeding, stable intermediate ryegrass for use as a short lived, improved turfgrass on golf courses and other areas using seeded turfgrasses.

BACKGROUND OF THE INVENTION

Annual ryegrass (*Lolium multiflorum*) and Perennial ryegrass (*Lolium perenne*) are the two most widely used turfgrasses in the world. Many varieties of each species have been developed. Perennial ryegrass is used as both a turfgrass and a forage grass. Annual ryegrass is used as a forage grass and a turfgrass, but there are no commercially available varieties of turf type annual ryegrass.

For many turf applications, a stable variety of Intermediate ryegrass if available would be desirable. Intermediate ryegrasses are crosses between annual and perennial ryegrass. This cross is relatively easy to make and has been frequently done. However, once the cross has been made, the resulting plants are not stable and true breeding, but revert to annual or perennial types.

For many southern golf courses planted with Bermuda grass, a standard practice is to overseed every fall with perennial ryegrass. Perennial ryegrass provides an outstanding turf cover during the cool winter months. However, perennial ryegrass is very persistent and does not easily die out and give way for the re-emerging Bermuda grass in the spring when warm weather returns.

Annual ryegrass, such as the variety 'Gulf', can also be used to overseed dormant Bermuda grass, but the turf quality is poor and not acceptable to most golf courses. However, annual ryegrass does die off quickly in the spring to make way for the re-emerging Bermuda grass.

What turf managers need for many applications is a cultivar that combines the turf quality and color of perennial ryegrass with the annual nature of annual ryegrass.

In northern turf areas, turf managers have long used annual ryegrass as a short-lived "nurse" grass for quick establishment when mixed with Kentucky bluegrass or red fescue. The annual ryegrass establishes very quickly and stabilizes the soil with a very quick ground cover establishment. Unfortunately annual ryegrass is very competitive in establishment and a very undesirable appearing species as a turfgrass.

What northern turf managers need for "Nurse grass" situations is an attractive fast starting short lived ryegrass that provides a high quality turf surface that allows early establishment but dies back to allow the slower establishing but long lived perennial grasses such as Kentucky Bluegrass and red fescue to then take over.

Crosses between annual ryegrass and perennial ryegrass have been made in attempts to develop Intermediate ryegrasses. Some varieties that have been developed include Oregreen, Transtar, Froghair, Interim and Transit. To date, none of these varieties of Intermediate ryegrass have been stable and true breeding. These intermediate rye grass varieties have all reverted to annual ryegrass during seed production increase since they have not been stable and true breeding.

Eight Species of the genus Lolium have been described. All but *L. perenne* have an annual life cycle, or at least are very short lived perennials. The genus Lolium is not complicated with naturally occurring polyploids; all species are diploid. Worldwide, *L. perenne* and *L. multiflorum*, are the most important species of the genus. Common names are perennial ryegrass for *L. perenne*, and Italian or annual ryegrass for *L. multiflorum*.

*L. perenne* and *L. multiflorum* hybridize readily. In fact, natural and bred hybrids among the three outcrossing ryegrass species, *L. multiflorum*×*L. perenne* (=*L.*× *hybridum*), *L. multiflorum*×*L. rigidum*; and *L. perenne*×*L. rigidum*, have been reported in Australia and Europe. Sufficient crossing occurs between the outcrossing Lolium species to form a wide range of fertile hybrids.

A seedling root fluorescence (SRF) test has been the official method for separation of ryegrass kinds of the International Seed Testing Association (ISTA) since 1953 (Jones, 1983, ISTA, 1966). The routine use of the seedling root fluorescence test in the United States started approximately in 1941. This policy provided that a SRF test shall be made on all ryegrass samples for which the species is to be determined. After experimenting with various light sources, test length, and the lifting of seedlings, standard procedures for conducting fluorescence tests were proposed. The extracted pigment responsible for root fluorescence in annual ryegrass is a weak, basic alkaloid, only slightly soluble in water. It was named annuloline. Other tests have been used to attempt a more conclusively way to separate the two important ryegrass species. Morphologically, leaf vernation differences between perennial and annual ryegrass have been used. Other methods applying biochemical characters, such at electrophoresis on general seed proteins and isozymes have yielded good results. Like the SRF test, however, such alternative tests have not been supported by genetic linkage studies.

On a morphological test basis, leaf vernation is considered to be the most accurate seedling characteristic used for distinguishing annual from perennial ryegrass. The Oregon Seed Trade Association (OSTA) considered using this character as a supplement to the fluorescence test when monitoring seed lots for certified status.

Little mention is made of Intermediate ryegrass in the ryegrass literature. For example, the 1995 OECD List of Cultivars Eligible for Certification in 1995 lists over 200 varieties of Perennial Ryegrass and Annual Ryegrass but no varieties of Intermediate ryegrass. The inherent instability of Intermediate ryegrass has made the development of these type of ryegrasses very difficult.

DETAILED DESCRIPTION OF THE INVENTION

In the description and tables which follow, a number of terms are used. In order to provide a clear and consistent understanding of the specification and claims, including the scope to be given such terms, the following definitions are provided:

Annual Ryegrass: *Lolium multiflorum*. A grass species commonly used as a turf grass that lives for one year or less.

Perennial Ryegrass: *Lolium perenne*. A grass species commonly used as a perennial turfgrass in the north and as a short-lived (less than one year) turfgrass to overseed warm season grasses.

Intermediate Ryegrass: *Lolium hybridum*. A grass species developed by crossing annual and perennial ryegrass. This is a "man-made" species which is not found in nature.

Turf: A covering of mowed vegetation usually a turfgrass, growing intimately with an upper stratum of intermingled roots and stems.

Turfgrass: A species or cultivar of grass, which is maintained as a mowed turf.

Turf Color: The composite visual color of a turfgrass community as perceived by the human eye. Usually measured on a 1 to 9 scale, with 9 being darkest.

Turf Quality: The degree to which a turf conforms to an agreed standard of uniformity, density, texture, growth, habit, smoothness, and color, as judged by subjective visual assessment. Usually measured on a 1–9 scale, with 9 being best.

Turfgrass Density: The number of turf grass tillers or shoots per unit area and measured at a certain time (e.g., days) after seeding.

Turfgrass Environment: The complex of climate, endaphic, biotic, and cultural (management) factors that act upon a turfgrass community and ultimately determine it's form and survival.

True Breeding: As used herein, the term "true breeding" means the ability of a variety to produce seed for three or more generations that reproduces the described characteristics of the variety and meets accepted Standards of Uniformity as defined by the Oregon State Seed Certification Handbook 2000 (Seed Certification Handbook 2000, Oregon State University Certification Board, Oregon State Extension, pp 1–5, (2000))

Leaf Texture: The relative fineness or coarseness of turfgrass leaves measured in millimeters at the cut or mowed leaf blade and measured at 6 weeks after seeding.

Flag Leaf Width: The width of a flag leaf blade measured at the ligule.

Flag Leaf: The first leaf below the seed head.

Plant Height: The height of a fully headed unmowed plant measured from the ground to the tip of the tallest seed head.

Seed Size: The relative size of seeds usually measures by determining the number of seeds per pound.

1000 Seed Weight: A standard measurement for seed determined by weighting 1000 pure, whole, seeds of a variety.

Seedling Vertical Growth Rate: The vertical growth rate of seedlings determined by measuring the height of the longest expanded leaf (tallest leaf) and measured at 6 weeks after seeding.

Munsell Color Chart: The Munsell System of color notation is essentially a scientific concept for describing and analyzing color in terms of three attributes called Hue, Value, and Chroma. These attributes are arranged in orderly scales of equal visual steps. a) Hue: Chromatic colors in the system are divided into five principal classes, which are given the Hue names of red, yellow, blue, and purple. A further sub-division yields the five intermediate Hue names of yellow-red, green-yellow, yellow-blue, etc., these being combinations of the five principal hues. For even finer sub-division each of these ten hues is divided into ten steps each (1 Red to 10 Red, etc.) thus increasing the hue range to 100. Hence the Hue notation of any color indicates its relationship to the five principal and five intermediate Hues. It is written as a capital letter (R for red, etc.) preceded by its appropriate number. b) Value: The value notation indicates the degree of lightness or darkness of a color in relation to a neutral gray scale, which extends from a theoretically pure black symbolized as "0/" to a theoretically pure while symbolized as "10/". A gray or a chromatic color that appears visually halfway in lightness between pure black and pure white has a value notation of "5/". Lighter colors are indicated by numbers ranging above five while darker colors are indicated by numbers below five. c) Chroma: The Chroma notation of a color indicates the strength (soluration) or degree of departure of a particular Hue from a neutral gray of the same value. The Chroma scale extends from "/0" for a neutral gray out to 10, 12, 14 or farther, depending upon the saturation of that particular color.

The new intermediate ryegrass varieties of this invention are uniform and stable, and also have a plant height, leaf texture, flag leaf length, seedling vertical growth and turf density that is more similar to perennial ryegrass versus other previously available intermediate and annual ryegrasses. These characteristics provide a uniform, true breeding and overall superior intermediate ryegrass for turfgrass purposes.

Varieties of the invention can be produced from seed. The invention includes seed producing an intermediate ryegrass variety selected from the group including or consisting of Transist, A-97 and A-98. Such seed includes seed that has been deposited in the American Type Culture Collection.

EXAMPLES

The following examples are provided to further illustrate the present invention and are not intended to limit the invention beyond the limitations set forth in the appended claims.

Example 1

Development of Transist

In 1991 the breeding research program that resulted in the intermediate variety, Transist was started. The following breeding history describes the procedures used:

In November, 1991 seeds were germinated from diploid annual ryegrass, variety not stated lots. Specifically three seed lots were used. Their numerical designations were L75-0-57, L43-1-160A, and L76-1-82A. Seeds were also germinated from the cultivar Transit, lot M22-9-87. Two hundred seedlings from each seed lot were transplanted into individual cell pack greenhouse flats. In January, 1992 the best tillered, darkest green plantlets were selected within and between the seed lots. Ultimately 22 plants were selected for $C_1$ crossing. The selected number of plants by lot number were: L75-0-57=6 plants, L43-1-160A=7 plants, L76-1-82A=4 plants, and Transit=5 plants.

In February, 1992, 2 ramets of each selection were made, and in April these were transplanted to a crossing nursery. The selections were surrounded by perennial rye grass individuals of half-sib families sourced from parental material of the following cultivars: Delaware Dwarf, Cutter, Tara, and Lynx.

In early May, 1992 the selected annual ryegrass plants expressed reproductive spikes. These were clipped. By the third week of May, spikes had been re-initiated and these synchronized with the spike expression of perennial ryegrass individuals. By May 28, all plants were at or near full flowering. The perennial ryegrasses were allowed to topcross the annual selections. Once seed was ripe in early July, only seed from each annual maternal line was harvested.

Seed yields were assessed for each maternal line. It was determined that 16 parents were superior over the other 6 in seed production. Thus, 16 half-sib families were carried forward in the program.

One hundred-fifty progeny seedlings of each of the selected half-sib families were established in cell pack greenhouse flats in early January, 1993. As the seedlings developed into tillered plants, each progeny was evaluated for leaf vernation. Any individuals that had folded vernation were discarded. Thirty-five percent of the plants were discarded based on this characteristic. The remaining plants were transplanted to a field nursery on Mar. 18, 1993. They were established as individual plants, spaced 30 cm apart within and between rows. The nursery was also established with perimeter and center rows of progenies from the perennial ryegrass cultivars Brightstar and Palmer II. These perennial ryegrass plants allowed an additional cycle of topcrossing in May, 1993.

In July, 1993, seed was harvested and bulked of individuals within the 16 half-sib families. Prior to anthesis, each family had been rogued for individuals within that did not express high seed production potential. Individuals were also discarded if they expressed perennial ryegrass phenotypic characteristics. These would include characters such as long outer spikelet glumes and awnless lemmas. The lightest green, widest foliaged plants were also rogued out of the population. Approximately 30% of individuals within families were discarded based on these criteria.

Progeny of the $C_2$ topcrossing were again established in greenhouse flats. The 16 families were kept separate, and 150 plants from each were cultured. Approximately 40% of the established plants were later discarded in the greenhouse due to displaying folded leaf vernation. The remaining progeny was transplanted to the field in March, 1994. Individuals of the perennial ryegrasses had been kept in place from the previous year. These were the $C_3$ topcross parents. Families were again rogued against individuals showing perennial ryegrass phenotypic, reproductive characteristics. Seed was harvested and bulked for individuals within each family.

After seed yields were calculated, poorest seed production families were discarded. Consequently, 11 families remained. A bulk was made using an equal weight of seed from each remaining family. These constituted synthetic generation 0 seed.

Recurrent bulk populations of the pre-breeder seed were established anew annually in 1994, 1995, and 1996. These represented seed increases for synthetic generations 1, 2, and 3. Each of the three seasons involved establishing greenhouse growouts and discarding individuals having folded leaf vernation. A high frequency of semi-rolled vernation typed were seen in the 1994 greenhouse growout. Consequently, these and all folded types were discarded. Four hundred individuals remained from a 2000 plant growout. The frequency of semi-rolled and folded types in 1995 and 1996 was 4–5%.

For the three years of recurrent bulk seed increase, off-type plants were rogued from the populations. This amounted to a frequency of 35%, 25%, and 18% respectively for the three seasons. The synthetic generation 3 seed produced in 1997 was breeder seed. The breeder of Transist has observed foundation and certified increase fields during 1998 and 1999. The cultivar is stable and uniform without the appearance of any significant frequency of variants, and only showing a trace amount of off-type plants.

This method resulted in the variety Transist and also continued. to produce additional new cultivars in later generations. For example, the 1997 recurrent reselection (A-97) shows further improvement in turf characteristics over Transist. These unexpected and surprising results continue to produce new improved types, as the 1998 generation (A-98) also is an excellent improved intermediate ryegrass type.

Table 8 summarizes some of the continued improvements in overall turf quality that produced better new turfgrasses that are superior to Transist. The results in Table 8 are a summary of a 1998–99 overseeding trial at Mississippi State University. These trials, and all other turf trials, measured the quality of turf by using visual ratings comparing the attributes of many varieties. The "Turfgrass Quality" is measured separately.

In all of these characteristics A-97, which is a further development from Transist, demonstrated significant improvement over Transist.

Example 2

Development of A-97 from Transist

In June, 1997, 18 vigorous darker green parental clones were selected from the breeder seed increase of Transist. The selections were removed pre-anthesis. The 18 parents were allowed to inter-pollinate in an isolated area free of flowering ryegrass. At seed maturity, the seed produced by each mother clone was harvested separately, conditioned and weighed. Because of low seed production, six of the original parents were eliminated from further increase. A progeny test of the remaining 12 parents was established in February, 1998. During the spring and early summer 1998, uniformity between half-sib families was excellent. A total of 12% of individuals from this test were removed pre/post anthesis. Most of the rouged individuals were too early in heading, or produced low numbers of reproductive seed spikes. The resulting seed (harvested as a bulk) was used to plant an early generation overseeding turf trial at Mississippi State University in October, 1998. A sample of the seed remaining was germinated and a bulked individual spaced planted nursery was established at PSW in February, 1999. During April and May, a total of eight percent individuals were removed from this nursery. The rogued plants were coarser in leaf texture and lighter in foliage color than the mean of the population. Seed was harvested as a bulk on Jul. 19, 1999. This was considered breeder seed of the experimental line. A sample of this seed was used to enter the line in the 1999/2000 On-site Overseeding trial sponsored by the National Turfgrass Evaluation Program. The remaining quantity (excluding a record sample) was used to establish an experimental foundation seed increase of the new cultivar.

Example 3

Development of A-98 from Transist

After breeder seed was harvested of Transist in 1997, the nursery was crewcut mowed, fertilized and allowed to initiate regrowth. In November, 1997, eighteen clones were selected from the nursery. These clones exhibited the densest fall regrowth, darkest foliage color and finest leaf texture than the mean of the population.

The 18 selected clones were transplanted to an isolated area away from other ryegrass plants. In May, 1998, it was evident that three of the 18 clones were not going to nick the anthesis date. Therefore, the three were removed from the isolation nursery. The remaining 15 clones were allowed to interpollinate. Mature seed was harvested and kept separate by maternal line. Seed from each mother was conditioned and weighed. Since there was not considerable difference in seed production among the maternal lines, and because the source germplasm was selected from an advanced breeding population of plants, progeny testing on a half-sib family basis was not done. Rather equal quantities of seed from each of the 15 mothers were bulked.

An increase nursery was transplanted to the field in March, 1999 of progeny from the 15 clone bulk seed lot. As the nursery came into reproductive heading growth stage, 7% of the individuals were discarded due to being lighter green in foliage color, weaker in overall tillering capacity, more prostrate in growth form, and earlier in heading date than the mean of the population. On May 23, the entire nursery was mowed to a 12 cm stubble height. The nursery was fertilized and irrigated to initiate rapid regrowth. The resulting regrowth was extremely uniform along with the timing of second crop reproductive spikes. An additional 2% of the individuals were removed prior to anthesis on the basis of light foliage color, prostrate growth, or by the production of limited number reproductive spikes. The nursery was allowed to mature seed, and bulk harvest was done on Aug. 2, 1999. An additional 11% of individuals were removed from the bulk harvest based upon showing spikes without floral awns. The bulk seed harvest represented breeder seed of the cultivar Pick Lh A-98.

Example 4

Transist is the first variety of intermediate ryegrass with a darker leaf and turf color more similar to perennial ryegrass. Color refers to the relative darkness or lightness of green color of the leaf blades of individual plants and in turf. A darker color is considered to be more desirable for turfgrass because it is more pleasing to the eye and dark colored turf can be fertilized less.

Turf color is evaluated two ways. a) In Table 1, the relative color of different varieties was scored using a 1–9 visual scale with 9 being darkest and 1 being the lightest green. Table 1 shows comparisons between the intermediate ryegrass Transist and other ryegrasses. b) Various standardized color charts are used to categorize turf that is measured by comparing actual turf color to standard colors. An example of this is the Munsell Color Charts which was used with Transist. Table 2 lists Transist and A-97 of the present invention versus other ryegrass varieties.

Both visual ratings and color chart comparisons (Tables 1 and 2) show clearly that Transist has a darker green (more desirable) color than annual ryegrass or other previous intermediate ryegrasses. The turf color of Transist is more similar to perennial ryegrass, Pennfine.

In Table 1 shown below, the visual color comparisons are given for several varieties taken in Tangent, Oregon during 1998 and 1999. The ratings are based on the following: 1=Light Green; 2=Medium Green; 3=Dark Green; and 4=Blue Green.

TABLE 1

Visual Color Comparisons
Tangent, Oregon - 1998/1999

| Variety | Rating |
| --- | --- |
| Pennfine | 2.5 |
| Transist | 2.5 |
| Linn | 2.2 |

TABLE 1-continued

Visual Color Comparisons
Tangent, Oregon - 1998/1999

| Variety | Rating |
| --- | --- |
| Froghair | 1.4 |
| Transtar | 1.3 |
| Gulf | 1.0 |
| LSD .05 | .5 |

In Table 2 shown below, the Munsell Color Chart readings are given are given for several varieties taken in Tangent, Oreg. during March, 2000.

TABLE 2

Munsell Color Chart Readings
Tangent, OR - March, 2000

| Variety | Page | Chroma | Value |
| --- | --- | --- | --- |
| Pennfine | 7.5 G/Y | 3.9 | 4.7 |
| Linn | 5.0 G/Y | 3.7 | 4.6 |
| Froghair | 7.5 G/Y | 3.9 | 4.3 |
| Gulf | 5.6 G/Y | 4.0 | 5.4 |
| Transist | 7.5 G/Y | 3.6 | 4.1 |
| A-97 | 7.5 G/Y | 3.5 | 4.0 |

Example 5

The varieties of the present invention are the first varieties of intermediate ryegrass with a finer leaf texture and smaller flag leaf widths more similar to perennial ryegrass. Leaf texture is the term used to describe the relative fineness or coarseness of grass leaves. A finer leaf texture is considered more desirable in turf as it results in a more attractive appearance. A wider or coarser leaf texture is less desirable because the appearance is less attractive. Leaf texture measurements in Tables 3 and flag leaf widths in Table 4 from 1998 and 1999 show that Transist has a significantly finer leaf texture and flag leaf width than any other variety of intermediate or annual ryegrass (Gulf). The leaf texture of Transist is more similar to the perennial ryegrass check varieties Pennfine and Linn but is still significantly wider than these perennial ryegrass varieties.

In Table 3 shown below, the leaf texture (in millimeters) of fully expanded tiller leaves at six weeks after planting are given for several varieties.

TABLE 3

Leaf Texture
Six weeks after planting

| Variety | Leaf Texture (mm) |
| --- | --- |
| Gulf | 5.62 |
| Transtar | 5.14 |
| Froghair | 5.01 |
| Linn | 3.83 |
| Transist | 3.73 |
| Pennfine | 3.11 |
| LSD .05 | .4 |

In Table 4 shown below, the flag leaf widths (in millimeters) are given for several varieties from data collected in 1998 and 1999.

TABLE 4

Flag Leaf Widths
1998/1999

| Variety | Flag Leaf Width (mm) |
| --- | --- |
| Transtar | 5.94 |
| Gulf | 5.91 |
| Froghair | 5.64 |
| Transist | 4.34 |
| Linn | 3.82 |
| Pennfine | 3.47 |
| LSD .05 | .63 |

Example 6

Transist is also the first cultivar of intermediate ryegrass that has a shorter plant height more similar to perennial ryegrass. Annual ryegrass grows significantly taller than perennial ryegrass. In turf situations a lower growth habit is more desirable because: a) Faster vertical growth results in more frequent mowing, and b) more total clippings are produced. For turf purposes a faster growth rate and more total clippings are not desirable.

As Table 5 shows, Transist is significantly shorter than any other variety of intermediate or annual ryegrass. Transist is closer to perennial ryegrass in plant height but is significantly taller than the check varieties Pennfine and Linn.

In Table 5 shown below, the mature plant height (in centimeters) are given for several varieties.

TABLE 5

Mature Plant Height
1998/1999

| Variety | Plant Height (cm) |
| --- | --- |
| Transtar | 100.5 |
| Froghair | 98.2 |
| Gulf | 93.6 |
| Transist | 81.9 |
| Linn | 72.0 |
| Pennfine | 66.4 |
| LSD .05 | 8.4 |

Example 7

Transist is the first intermediate ryegrass that has a reduced rate of vertical growth more similar to perennial ryegrass. Annual ryegrass grows significantly faster and taller than perennial ryegrass. A slower growth rate more similar to perennial ryegrass is highly desirable because there is less need for frequent mowing and slower growing turf has a higher quality than faster growing turf. All other intermediate ryegrasses developed to date have growth rates more similar to annual ryegrass.

Table 6 shows Transist has a slower rate of vertical growth than annual ryegrasses and other intermediate ryegrasses. Transist has a much reduced growth rate more similar to perennial ryegrass. This makes Transist a much more desirable turfgrass than annual ryegrasses or other intermediate ryegrasses. In Table 6 shown below, the seedling vertical growth rate (in millimeters) is given for the length of the longest expanded leaf, are given for several varieties.

TABLE 6

Seedling Vertical Growth Rate

| Variety | Length of Longest Expanded Leaf (mm) |
| --- | --- |
| Gulf | 35.8 |
| Froghair | 31.1 |
| Transtar | 30.9 |
| Linn | 22.2 |
| Transist | 18.9 |
| Pennfine | 15.0 |
| LSD .05 | 3.8 |

Example 8

Transist is the first intermediate ryegrass with a smaller seed size more similar to perennial ryegrass. Seed size is an important characteristic in the overseeded turf industry for two reasons: a) A smaller seed size results in better distribution and penetration of seed into the turf being over seeded. A smaller seed is more easily placed deeper into the turf cover and nearer to the ground for better germination and establishment; and b) a smaller seed size means more seeds per pound so that smaller amounts of seed applied will result in more seeds to germinate and establish per unit area.

Annual ryegrass has a much larger seed than perennial ryegrass which makes annual ryegrass much less desirable for overseeding purposes. Other varieties have similar seed sizes to annual ryegrass as shown in Table 7. However, Table 7 shows, Transist has a much smaller seed than annual ryegrass or other intermediate ryegrasses making it a much more desirable overseeding turfgrass. In Table 7 shown below, the 1000 seed weights (in grams) are given for several varieties.

TABLE 7

1000 Seed Weights
1998/1999

| Variety | 1000 Seed Weights (gm) |
| --- | --- |
| Transtar | 3.018 |
| Gulf | 3.050 |
| Froghair | 3.035 |
| Linn | 2.422 |
| Transist | 2.244 |
| Pennfine | 1.818 |
| LSD .05 | .5 |

Example 9

Transist, A-98 and A-97 are the first intermediate ryegrasses with improved turf density more similar to perennial ryegrass. Turf density is an important characteristic in determining the overall quality of a turf. Turf density is measured in number of tillers per 100 square centimeters. The higher the number of tillers, the better the turf quality, utility and appearance. Turf type perennial ryegrass has a much higher turf density than annual type ryegrasses. This means the turf quality of perennial ryegrass is much higher than annual.

As shown in Table 8, Transist, A-98 and A-97 are the first varieties of intermediate ryegrass that have a turf density more similar to perennial ryegrass. All of the other intermediate ryegrasses tested had turf densities similar to annual ryegrass.

Table 8 shows Transist is much more similar in turf density to perennial ryegrasses such as Pennfine. All the other intermediate ryegrasses tested had much lower turf density and were similar to annual ryegrass.

In Table 8 shown below, the turf density of several varieties are given in tillers/100 cm$^2$.

TABLE 8

Turf Density

| Variety | Turf Density (tillers/100 cm$^2$) |
| --- | --- |
| Pennfine | 121 |
| Transist | 110 |
| A-98 | 106 |
| A-97 | 103 |
| Linn | 98 |
| Gulf | 88 |
| Froghair | 82 |
| Interim | 82 |
| Transtar | 74 |
| LSD .05 | 32 |

Example 10

In Table 9 shown below, head to head comparisons with the instant invention, Transist, A-97 and Gulf Annual Ryegrass are shown for several traits including turf color, turf quality, leaf texture and turf density. This information was collected at the Mississippi State University Trial from 1998/1999. Figures shown are 1=poor and 9=best. The intermediate ryegrass varieties of the present invention, Transist and A-97, show significant differences versus the annual ryegrass variety Gulf.

TABLE 9

Head to Head Comparisons of Transist, A-97 and Gulf Ryegrasses Mississippi State University Trial 1998/1999

| Trait | Transist | A-97 | Gulf Ryegrass |
| --- | --- | --- | --- |
| Turf Color | 5.4 | 6.0 | 3.9 |
| Turf Quality | 5.2 | 5.8 | 3.6 |
| Leaf Texture | 5.1 | 5.7 | 3.7 |
| Turf Density | 5.1 | 5.8 | 3.1 |

Intermediate ryegrass seeds of Transist, A-97 and A-98 have been placed on deposit with the American Type Culture Collection (ATCC), Manassas, Va., under Deposit Accession Numbers PTA-2255, PTA-2257 and PTA-2256 on Jul. 24, 2000.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A true breeding intermediate turfgrass variety having the identifying characteristics of a variety selected from the group consisting of: Transist deposited under American Type Culture Collection accession number PTA-2255; A-97 deposited under American Type Culture Collection accession number PTA-2257, and A-98 deposited under American Type Culture Collection accession number PTA-2256.

2. Seed of the variety of claim 1.

3. A turfgrass plant, or parts thereof, produced by growing the seed of claim 2.

4. Pollen of the plant of claim 3.

5. An ovule of the plant of claim 3.

6. A turfgrass plant, or parts thereof, having all of the physiological and morphological characteristics of the turfgrass plant of claim 3.

7. An intermediate ryegrass produced by growing seed from the intermediate ryegrass of claim 3.

8. An intermediate ryegrass produced vegetatively from the intermediate ryegrass of claim 3.

9. A method for producing a hybrid turfgrass seed comprising crossing a first parent turfgrass plant with a second parent turfgrass plant and harvesting the resultant hybrid turfgrass seed, wherein said first parent turfgrass plant or said second parent turfgrass plant is the turfgrass plant of claim 3.

10. A hybrid turfgrass seed produced by the method of claim 9.

11. A hybrid turfgrass plant, or parts thereof, produced by growing said hybrid turfgrass seed of claim 10.

12. A method for developing an intermediate turfgrass plant in a turfgrass plant breeding program using plant breeding techniques which include employing a turfgrass plant, or its parts, as a source of plant breeding material comprising: using the turfgrass plant, or its parts, of claim 3 as a source of said breeding material.

* * * * *